United States Patent [19]

Hiratani

[11] Patent Number: 5,071,989

[45] Date of Patent: Dec. 10, 1991

[54] QUINOLYL MALONAMIDE DERIVATIVES

[75] Inventor: Kazuhisa Hiratani, Tsukuba, Japan

[73] Assignee: Director-General of Agency of Industrial Science and Technology, Japan

[21] Appl. No.: 658,586

[22] Filed: Feb. 21, 1991

[51] Int. Cl.⁵ .......................................... C07D 403/12
[52] U.S. Cl. .................................................. 546/171
[58] Field of Search ......................................... 546/171

Primary Examiner—David B. Springer
Attorney, Agent, or Firm—Lorusso & Loud

[57] ABSTRACT

A malonamide derivative expressed by the following general formula (I):

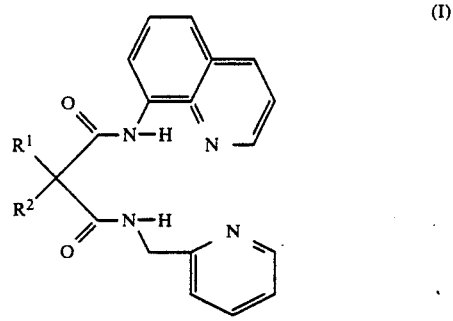

wherein $R^1$ and $R^2$ stand, independently from each other, for a hydrogen atom, an alkyl group, an aralkyl group or an aryl group. The malonamide derivative is useful as an ionophore which can selectively transport cupric ions through liquid membranes.

5 Claims, 1 Drawing Sheet

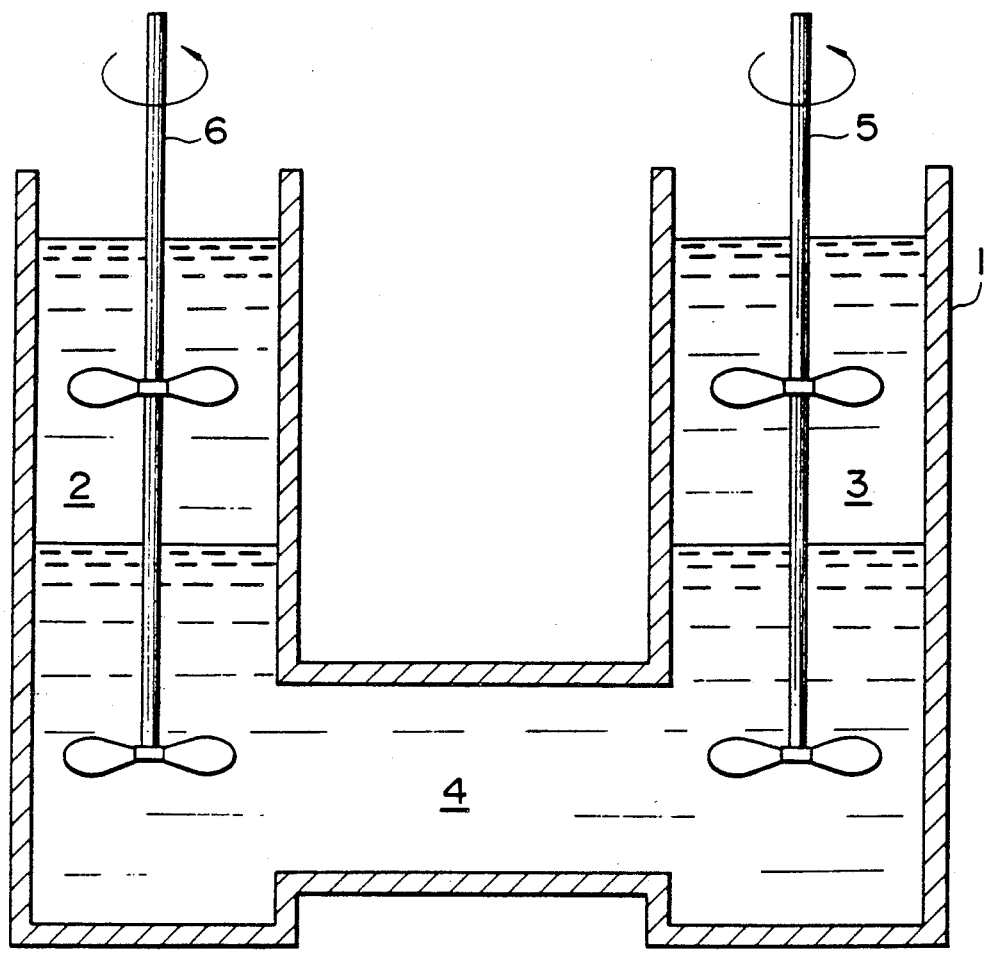

QUINOLYL MALONAMIDE DERIVATIVES

BACKGROUND OF THE INVENTION

This invention relates to novel malonamide derivatives useful as an ionophore. The present invention is also directed to a method for selectively transporting cupric ions contained in a first liquid to a second liquid using the above malonamide.

Separation of cupric ions from other heavy metal ions is a very important technique utilized for the recovery and concentration thereof. There are a lot of known extractants and ion transporting agents (ionophores) used for the separation of specific metal ions. An ionophore to be utilized for continuously transporting specific ions contained in a first liquid to a second liquid is required to selectively capture cupric ions. In addition, it is important that the ionophore should release the captured ions to the second liquid in order to effectively perform the continuous transportation of the ions. Known extractants and ionophores, however, are not satisfactory for cupric ions with respect to selectivity or efficiency.

SUMMARY OF THE INVENTION

It is, therefore, the prime object of the present invention to provide a novel malonamide derivative useful as an ionophore and capable of continuously transporting cupric ions contained in a liquid to another liquid.

Another object of the present invention is to provide a malonamide derivative of the above-mentioned type which can transporting cupric ions contained in a first liquid to a second liquid even when the concentration of the cupric ions in the first liquid is lower than that in the second liquid.

It is a further object of the present invention to provide a method for transporting cupric ions from a liquid to another liquid.

In accomplishing the foregoing objects, there is provided in accordance with the present invention a malonamide derivative expressed by the following general formula (I):

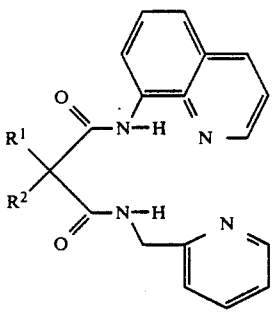

wherein $R^1$ and $R^2$ stand, independently from each other, for a hydrogen atom, an alkyl group, an aralkyl group or an aryl group.

The alkyl group represented by the symbol $R^1$ or $R^2$ is preferably a lower alkyl group having 2-8 carbon atoms. The aralkyl group represented by $R^1$ or $R^2$ is preferably a benzyl group, a phenylethyl group or a phenylpropyl group.

In another aspect, the present invention provides a method of transporting cupric ions in a first liquid to a second liquid, including a step of contacting a third liquid substantially immiscible with the first and second liquids and containing above malonamide derivative with the first liquid so that cupric ions in the first liquid are captured by the malonamide derivative, and a step of contacting the third liquid containing the cupric ions captured by the malonamide derivative with the second liquid so that the cupric ions captured by the malonamide derivative are released to the second liquid.

BRIEF DESCRIPTION OF THE DRAWING

Other objects, features and advantages of the present invention will become apparent from the detailed description of the invention to follow when considered in light of the accompanying drawing, in which the sole FIGURE is an elevational, cross-sectional view diagrammatically showing an apparatus useful for performing the cupric ion transportation using the malonamide derivative of the present invention.

DETAILED DESCRIPTION OF THE INVENTION

The malonamide derivative according to the present invention may be obtained in a manner known per se. For example, a malonic acid derivative of the formula (II):

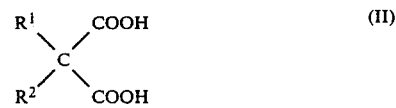

wherein $R^1$ and $R^2$ have the same meaning as above, is reacted with a halogenation agent such as thionyl chloride to obtain a malonic chloride of the formula (III):

The above reaction may be carried out a refluxing temperature of thionyl chloride.

The resulting acid dihalide of the formula (III) is then reacted with an equivalent of 8-aminoquinoline and the resulting product is subsequently reacted with an equivalent of 2-aminomethylpyridine, thereby to give the desired malonamide derivative of the formula (I). These amide-forming reactions may be carried out at a temperature of 0°-120 ° C., preferably 30°-80 ° C., in an inert solvent such as benzene, cyclohexane, chloroform, dioxane or tetrahydrofuran.

The malonamide derivative according to the present invention, when subjected to a neutral or a weakly acidic condition, i.e. a pH region of about 3-7, can capture cupric ions with a high selectivity. In an acidic condition of a pH range of about below 3, the malonamide derivative can liberate the captured cupric ions. Thus, the malonamide derivative of the present invention can serve to act as an ionophore or carrier for transporting cupric ions.

The transportation of cupric ions can be done by contacting a first, cupric ion-containing liquid, generally an aqueous liquid having a pH of about 3-7, preferably 5-7, with a third liquid, generally an organic solvent solution, containing the malonamide derivative of the present invention and substantially immiscible with the first liquid so that the cupric ions may be captured by the malonamide derivative. Illustrative of suitable organic solvents are halogenated organic solvents such as chloroform, carbon tetrachloride and dichloroethane; hydrocarbons such as benzene, toluene and xylene; and alcohols such as octanol and hexanol. The concentration of the malonamide in the third liquid is generally in the range of $10^{-5}$ to 1.0 mol/liter, preferably $10^{-3}$ to $10^{-1}$ mol/liter.

The third liquid thus containing the cupric ions captured by the malonamide derivative is then contacted with a second liquid, generally an aqueous acidic liquid having a pH of 3 or less, preferably 1-2, and substantially immiscible with the third liquid so that the captured cupric ions are liberated to the second liquid. The second liquid which is to receive cupric ions may be an aqueous liquid containing an inorganic acid such as hydrochloric acid, sulfuric acid or phosphoric acid or an organic acid such as formic acid, acetic acid or an organic sulfonic acid.

One example of cupric ion transportation method will now be described with reference to the accompanying drawing. Referring to the FIGURE, designated by the reference numeral 1 is a U-shaped vessel equipped with stirrer means 5 and 6 in the respective vertical portions thereof. A third, malonamide-containing liquid is contained in the vessel 1 to form a third layer 4 with its liquid level positioned adjacent to the respective lower portions of the vertical portions. A first, cupric ion-containing liquid and a second, acidic liquid are poured into the vessel 1 to form first and second layers 2 and 3, respectively, on the third layer 4.

In the interface at which the first and third layers 2 and 4 are contacted, cupric ions in the layer 2 are captured by the malonamide contained in the layer 4, while in the interface at which the second and third layers 3 and 4 are contacted, the cupric ions captured by the malonamide are liberated and released to the second layer 3. The stirrer means 5 and 6 are continuously operated to facilitate the capture and the liberation of cupric ions. In this method, the third layer 4 should, of course, have a higher specific gravity than the other layers 2 and 3.

If desired, a suitable membrane may be disposed between the first and third liquids and between the second and third liquid. In a special case, the malonamide derivative may be supported on a suitable support means such as a filter paper or a high molecular weight membrane and each side of the malonamide-supporting means is contacted with respective one of the first and second liquids. The transportation may also be effected by a usual extraction method in which the first and the third liquids are vigorously shaken together to extract the cupric ions with the third liquid, the cupric ions contained in the third liquid being subsequently extracted with the second liquid.

With the malonamide derivative according to the present invention, the transportation of cupric ions may be effected continuously at a very high rate. Further, even when the concentration of cupric ions in the first liquid is lower than that of the second liquid, the malonamide derivative of this invention can carry cupric ions from the first to the second liquid.

The following examples will further illustrate the present invention.

EXAMPLE 1

Preparation of Dibutyl-N-(8-quinolyl)-N'-(2-pyridylmethyl)-malonamide

A mixture containing 2.2 g (10 mmol) of dibutylmalonic acid and 5 ml of thionyl chloride was refluxed for 2 hours without using a solvent. Unreacted thionyl chloride was then removed in vacuo to leave dibutylmalonyl dichloride. This dichloride was added to a benzene solution containing 1.4 g (10 mmol) of 8-aminoquinoline and 1 g (10 mmol) of triethylamine and the mixture was stirred at room temperature for 4 hours. To the resulting mixture were subsequently added 1.1 g (10 mmol) of 2-aminomethylpyridine and 1 g (10 mmol) of triethylamine and the mixture was reacted at room temperature for 4 hours. The resulting mixture was washed with water, dried over anhydrous magnesium sulfate and distilled in vacuo for the removal of the solvent. The residue was then subjected to column chromatography to obtain 1.1 g of a colorless sticky liquid. The NMR, IR and MS spectra reveal that this product is dibutyl-N-(8-quinolyl)-N'-(2-pyridylmethyl)-malonamide (compound of the formula (I) in which $R^1$ and $R^2$ are each n-butyl). The yield is 27%. The mass analysis shows: Calculated: 432.252 ($C_{24}H_{32}N_4O_2$), Measured: 432.254.

EXAMPLE 2

Preparation of Benzyl-N-(8-quinolyl)-N'-(2-pyridylmethyl)-malonamide

Example 1 was repeated in the same manner as described except that 1.9 g (10 mmol) of benzylmalonic acid were substituted for 2.2 g of dibutylmalonic acid. Benzyl-N-(8-quinolyl)-N'-(2-pyridylmethyl)-malonamide (compound of the formula (I) in which $R^1$ is hydrogen and $R^2$ is benzyl) was obtained in an amount of 0.9 g (yield: 22%). The mass analysis: Calculated: 410.174 ($C_{25}H_{22}N_4O_2$),
Measured: 410.172.

EXAMPLE 3

Selective Transportation of $Cu^{++}$

The following first, second and third solutions were prepared:

First Solution: 15 ml of an aqueous solution (pH: 6.2) containing 10 mmol/liter of $Cu(OCOCH_3)_2$, 10 mmol/liter of $Ni(OCOCH_3)_2$, 10 mmol/liter of $Co(OCOCH_3)_2$ and 10 mmol/liter of $Zn(OCOCH_3)_2$;

Second Solution: 15 ml of an aqueous 0.1N sulfuric acid;

Third Solution: A solution obtained by dissolving $3\times10^{-4}$ mol of the compound obtained in Example 1 in 30 ml of chloroform.

These solutions were charged in an apparatus as shown in the FIGURE and the each of the solutions was stirred at 25° C. for two days. Atomic absorption analysis of the resulting second solution revealed that 104 μmol of cupric ions were transported thereto. Substantially no nickel, cobalt or zinc ions were detected.

EXAMPLE 4

Rate of Transportation of $Cu^{++}$

Example 3 was repeated in the same manner as described except that 15 ml of an aqueous solution (pH:

6.2) containing 10 mmol/liter of $Cu(OCOCH_3)_2$ was used as the first liquid and that the stirring was continued for 3 days. The amount of cupric ions in the second liquid was measured after 1, 2 and 3 days from the commencement of the test. The results were as summarized in Table 1. In Table 1, the transportation rate (R) is calculated according to the following equation:

$$R = \frac{\text{Amount of cupric ions in 2nd soln.} \times 100 \ (\%)}{\text{Amount of cupric ions orginally present in 1st soln.}}$$

TABLE 1

| Process Time (day) | 1 day | 2 days | 3 days |
|---|---|---|---|
| Amount of $Cu^{++}$ ($\mu$mol) | 84 | 122 | 144 |
| Transportation Rate R (%) | 56 | 81 | 93 |

COMPARATIVE EXAMPLES 1-4

Example 4 was repeated in the same manner as described except that $3 \times 10^{-4}$ mol of the malonamide compound obtained in Example 1 was replaced by $3 \times 10^{-4}$ mol of dibutyl-bis(8-quinolyl)malonamide (Comparative Example 1), $3 \times 10^{-4}$ mol of N,N'-bis(8-quinolyl)succinamide (Comparative Example 2), $6 \times 10^{-4}$ mol of 7-dodecyl-8-hydroxyqunoline (Comparative Example 3) or $3 \times 10^{-4}$ mol of N,N'-bis(-quinolyl)glutalamide (Comparative Example 4) and that the stirring was continued for 2 days. The amount of cupric ions transported to the second liquid after 2 days is shown in Table 2 together with the result of Example 4.

TABLE 2

|  | Amount of $Cu^{++}$ ($\mu$mol) |
|---|---|
| Example 4 | 122 |
| Comparative Example 1 | 3 |
| Comparative Example 2 | 23 |
| Comparative Example 3 | 50 |
| Comparative Example 4 | 95 |

The chemical formulas of the ionophores used in Comparative Examples 1-4 are shown below:

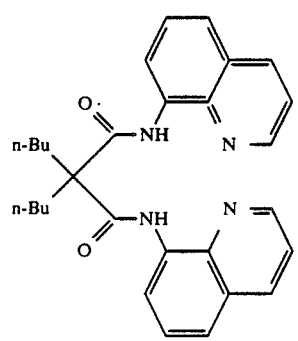

Comparative Example 1

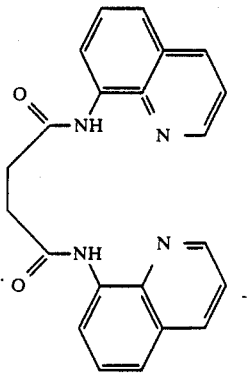

Comparative Example 2

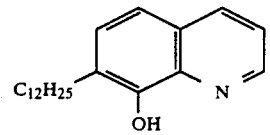

Comparative Example 3

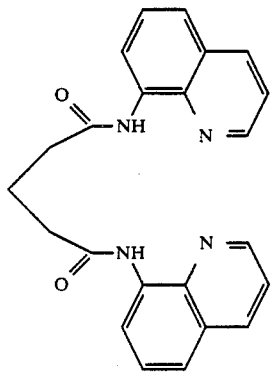

Comparative Example 4

EXAMPLES 5-7

Example 3 was repeated in the same manner as described except that 15 ml of an aqueous solution (pH: 6.2) containing 10 mmol/liter of $Zn(OCOCH_3)_2$ (Example 5), $Ni(OCOCH_3)_2$ (Example 6) or $Co(OCOCH_3)_2$ (Example 7) was used as the first liquid. No zinc ions, nickel ions or cobalt ions were detected in the second solution after 2 days stirring.

EXAMPLE 8

Rate of Transportation of $Cu^{++}$

Example 4 was repeated in the same manner as described except that a solution obtained by dissolving $3 \times 10^{-4}$ mol of the compound obtained in Example 2 in 30 ml of chloroform was used as the third liquid. The amount of cupric ions in the second liquid was measured after 1, 2 and 3 days from the commencement of the test. The results were as summarized in Table 3.

TABLE 3

| Process Time (day) | 1 day | 2 days | 3 days |
|---|---|---|---|
| Amount of $Cu^{++}$ ($\mu$mol) | 75 | 105 | 128 |
| Transportation Rate R (%) | 50 | 70 | 85 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A malonamide derivative expressed by the following general formula (I):

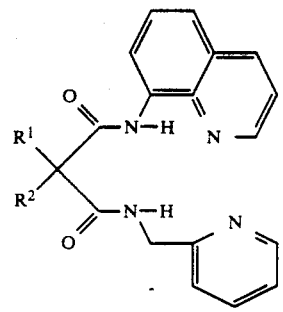

wherein $R^1$ and $R^2$ stand, independently from each other, for a hydrogen atom, an alkyl group, an aralkyl group or an aryl group.

2. A malonamide derivative as claimed in claim 1, wherein said alkyl group is a lower alkyl group having 2–8 carbon atoms.

3. A malonamide derivative as claimed in claim 1, wherein said aralkyl group is selected from the group consisting of a benzyl group, a phenylethyl group and a phenylpropyl group.

4. Di-n-butyl-N-(8-quinolyl)-N'-(2-pyridylmethyl)-malonamide.

5. Benzyl-N-(8-quinolyl)-N'-(2-pyridylmethyl)-malonamide.

* * * * *

UNITED STATES PATENT AND TRADEMARK OFFICE
CERTIFICATE OF CORRECTION

PATENT NO. : 5,071,989
DATED : December 10, 1991
INVENTOR(S) : Kazuhisa HIRATANI It is certified that error appears in the above-identified patent and that said Letters Patent is hereby corrected as shown below:

On the title page:

Please insert the following:

--Foreign Application Priority Data

July 19, 1990 [JP] Japan........................ 2-191307--

Signed and Sealed this

Eighth Day of June, 1993

Attest:

MICHAEL K. KIRK

Attesting Officer

Acting Commissioner of Patents and Trademarks